United States Patent
Johnson et al.

(10) Patent No.: US 9,642,670 B2
(45) Date of Patent: May 9, 2017

(54) RESONANT INVERTER WITH A COMMON MODE CHOKE

(71) Applicant: COVIDIEN LP, Mansfield, MA (US)

(72) Inventors: Joshua H. Johnson, Arvada, CO (US); James A. Gilbert, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 373 days.

(21) Appl. No.: 14/190,830

(22) Filed: Feb. 26, 2014

(65) Prior Publication Data

US 2015/0119871 A1    Apr. 30, 2015

Related U.S. Application Data

(60) Provisional application No. 61/897,107, filed on Oct. 29, 2013.

(51) Int. Cl.
*A61B 18/12* (2006.01)
*A61B 18/00* (2006.01)
*A61B 18/16* (2006.01)

(52) U.S. Cl.
CPC .......... *A61B 18/1206* (2013.01); *A61B 18/16* (2013.01); *A61B 2018/0063* (2013.01); *A61B 2018/00577* (2013.01); *A61B 2018/00589* (2013.01); *A61B 2018/00601* (2013.01)

(58) Field of Classification Search
CPC ............... A61B 18/1206; A61B 18/16; A61B 2018/00577; A61B 2018/00589; A61B 2018/00601; A61B 2018/0063
See application file for complete search history.

(56) References Cited

U.S. PATENT DOCUMENTS

| | | |
|---|---|---|
| 5,841,239 A | 11/1998 | Sullivan et al. |
| 6,939,347 B2 | 9/2005 | Thompson |
| D574,323 S | 8/2008 | Waaler |
| 8,685,015 B2 | 4/2014 | Gilbert |
| 2005/0177150 A1 | 8/2005 | Amoah |
| 2007/0129716 A1 | 6/2007 | Daw et al. |
| 2007/0173808 A1 | 7/2007 | Goble |
| 2010/0124035 A1 | 5/2010 | Bandholz et al. |
| 2012/0095461 A1 | 4/2012 | Herscher et al. |
| 2012/0119697 A1* | 5/2012 | Boys ............. B60L 11/182 320/108 |
| 2013/0023871 A1 | 1/2013 | Collins |

(Continued)

FOREIGN PATENT DOCUMENTS

| | | |
|---|---|---|
| DE | 179607 C | 3/1905 |
| DE | 390937 C | 3/1924 |

(Continued)

OTHER PUBLICATIONS

European Search Report for International Application No. EP14159838, dated Jun. 17, 2014, 3 pages.

(Continued)

*Primary Examiner* — Michael Peffley
*Assistant Examiner* — Samantha Good

(57) ABSTRACT

The present disclosure is directed to an electrosurgical generator including a tank configured to output energy and an H-bridge configured to drive the tank. The generator also includes a choke. The choke impedes a common mode current generated by the H-bridge and provides a leakage inductance for the tank.

8 Claims, 4 Drawing Sheets

(56) References Cited

U.S. PATENT DOCUMENTS

| | | |
|---|---|---|
| 2013/0267945 A1 | 10/2013 | Behnke, II et al. |
| 2014/0104028 A1 | 4/2014 | Johnston |
| 2015/0034406 A1 | 2/2015 | Hirose |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1064047 A1 | 1/2001 |
| EP | 1366724 A1 | 12/2003 |
| EP | 1 519 471 | 3/2005 |
| EP | 1776929 A1 | 4/2007 |
| EP | 2469699 A2 | 6/2012 |
| EP | 2742888 A1 | 6/2014 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 60-064765 | 4/1985 |
| JP | 63 005876 A | 1/1988 |
| JP | 2002-065690 A | 3/2002 |
| JP | 2005-185657 A | 7/2005 |
| JP | 2009-081183 A | 4/2009 |
| SU | 166452 | 11/1964 |
| SU | 727201 A2 | 4/1980 |
| WO | 96/39086 A1 | 12/1996 |
| WO | 9815317 A1 | 4/1998 |
| WO | 9947204 A1 | 9/1999 |
| WO | 02/11634 A1 | 2/2002 |
| WO | 02/45589 A2 | 6/2002 |
| WO | 03/090635 A1 | 11/2003 |
| WO | 2006/050888 A1 | 5/2006 |
| WO | 2008/053532 A1 | 5/2008 |
| WO | 2013-125010 A1 | 8/2013 |
| WO | 2014-062357 A1 | 4/2014 |

OTHER PUBLICATIONS

Wald et al., "Accidental Burns", JAMA, Aug. 16, 1971, vol. 217, No. 7, pp. 916-921.

Vallfors et al., "Automatically Controlled Bipolar Electrosoagulation-'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

Burdette et al. "In Vivo Probe Measurement Technique For Determining Dielectric Properties At VHF Through Microwave Frequencies", IEEE Transactions on Microwave Theory and Techniques, vol. MTT-28, No. 4, Apr. 1980 pp. 414-427.

Richard Wolf Medical Instruments Corp. Brochure, "Kleppinger Bipolar Forceps & Bipolar Generator", 3 pages Jan. 1989.

Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.

Geddes et al., "The Measurement of Physiologic Events by Electrical Impedence", Am. J. Ml, Jan. Mar. 1964, pp. 16-27.

Cosman et al., "Methods of Making Nervous System Lesions", In William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Benaron et al., "Optical Time-Of-Flight And Absorbance Imaging Of Biologic Media", Science, American Association for the Advancement of Science, Washington, DC, vol. 259, Mar. 5, 1993, pp. 1463-1466.

Cosman et at., "Radiofrequency Lesion Generation and Its Effect on Tissue Impedance", Applied Neurophysiology 51: (1988) pp. 230-242.

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . .", Journal of Applied Sciences-Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297, Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

(56) References Cited

OTHER PUBLICATIONS

Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/174,551 dated Feb. 6, 2014 inventor: Johnson.
U.S. Appl. No. 14/179,724 dated Feb. 13, 2014 inventor: Johnson.
U.S. Appl. No. 14/190,895 dated Feb. 26, 2014 inventor: Gilbert.
European Search Report No. 14159839.1 dated Jul. 8, 2014.

\* cited by examiner

RESONANT INVERTER WITH A COMMON MODE CHOKE

CROSS REFERENCE TO RELATED APPLICATION

The present application claims the benefit of and priority to U.S. Provisional Application Ser. No. 61/897,107, filed on Oct. 29, 2013, the entire contents of which are incorporated herein by reference.

BACKGROUND

1. Technical Field

The present disclosure relates to radiofrequency amplifiers that use phase-shifted full bridge resonant inverters. Particularly, the present disclosure is directed to reducing the cost and complexity of the resonant inverters and improving the performance of the resonant inverters.

2. Background of the Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. A source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated and the return electrode is placed remotely from the active electrode to carry the current back to the generator. In bipolar electrosurgery, one of the electrodes of the hand-held instrument functions as the active electrode and the other as the return electrode.

FIG. 1 is an example of a prior art electrosurgical generator that uses a phase-shifted full bridge resonant inverter to generate the electrosurgical energy needed to perform the electrosurgical procedure. The generator 100 includes a resonant inverter circuit 102 and a pulse width modulation (PWM) controller 108. The resonant inverter circuit 102 includes an H-bridge 104 an LCLC tank 106. However, in the electrosurgical generator 100, the transitioning of the FETs Q1, Q2, Q3, and Q4 may induce common mode currents that circulate through the resonant inverter circuit 102 causing electromagnetic compatibility (EMC) problems for the electrosurgical generator 100.

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As used herein, the term "generator" may refer to a device capable of providing energy. Such device may include a power source and an electrical circuit capable of modifying the energy outputted by the power source to output energy having a desired intensity, frequency, and/or waveform.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described data and/or algorithms may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

In an aspect of the present disclosure, an electrosurgical generator includes a tank configured to output energy and an H-bridge configured to drive the tank. The generator also includes a choke. The choke is configured to impede a common mode current generated by the H-bridge and provide a leakage inductance for the tank.

The choke includes a core having a central member, a primary winding wound about the central member, and a secondary winding wound about the central member. The primary winding and the secondary winding may include 10 to 15 turns. The primary winding is wound in a first direction while the secondary winding is wound in a second direction opposite the first direction. The distance between the primary winding and the secondary winding determines the leakage inductance of the choke.

In another aspect of the present disclosure, the choke includes a first core half having a first central member and a second core half having a second central member. A first bobbin is disposed about the first central member while a second bobbin is disposed about the second central member. A primary winding is disposed about the first bobbin and a secondary winding is disposed about the second bobbin.

The primary winding and the secondary winding may include 10 to 15 turns. The primary winding is wound in a first direction while the secondary winding is wound in a second direction opposite the first direction. The distance between the primary winding and the secondary winding determines the leakage inductance of the choke. The distance between the primary winding and the secondary winding may be adjustable.

In yet another embodiment of the present disclosure, a method of adjusting a leakage inductance of a choke is provided. The choke includes a first core half having a first central member, a second core half having a second central member, a first bobbin disposed about the first central member, a second bobbin disposed about the second central member, a primary winding disposed about the first bobbin, and a secondary winding disposed about the second bobbin. In the method, a distance between the primary winding and the secondary winding is changed to adjust the leakage inductance. The distance may be changed by moving the first bobbin relative to the second bobbin.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
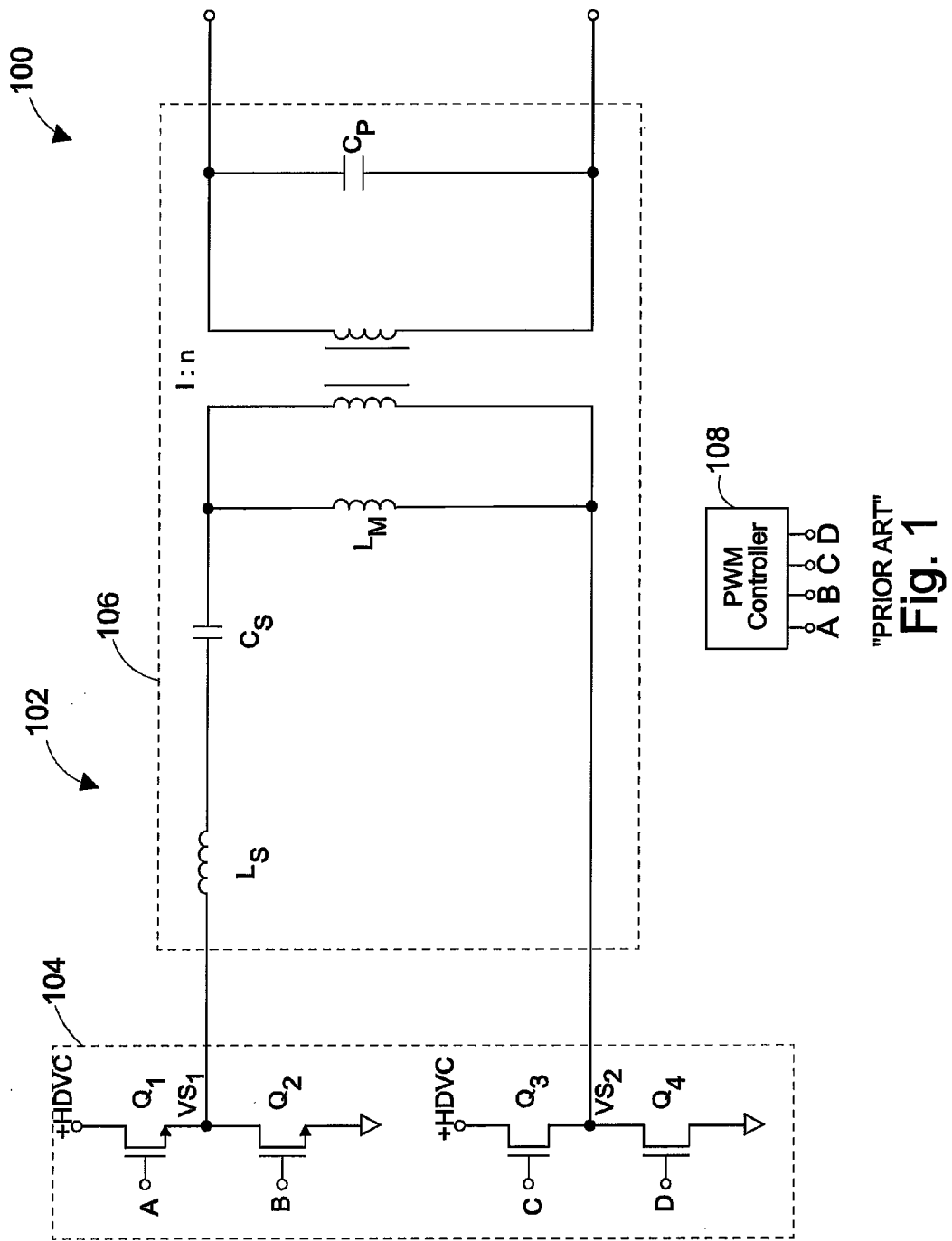
FIG. 1 is a schematic illustration of a prior art electrosurgical generator.

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

The present disclosure is directed to an electrosurgical generator that employs a phase-shifted full bridge resonant inverter having an LCLC tank topology and an H-bridge. In an embodiment of the present disclosure, the resonant inverter utilizes a common mode (CM) choke as a resonant component. The CM choke impedes CM currents generated by the H-bridge. The CM choke also functions as an energy storage element to reduce the number of components in the electrosurgical generator.

Figure 2:
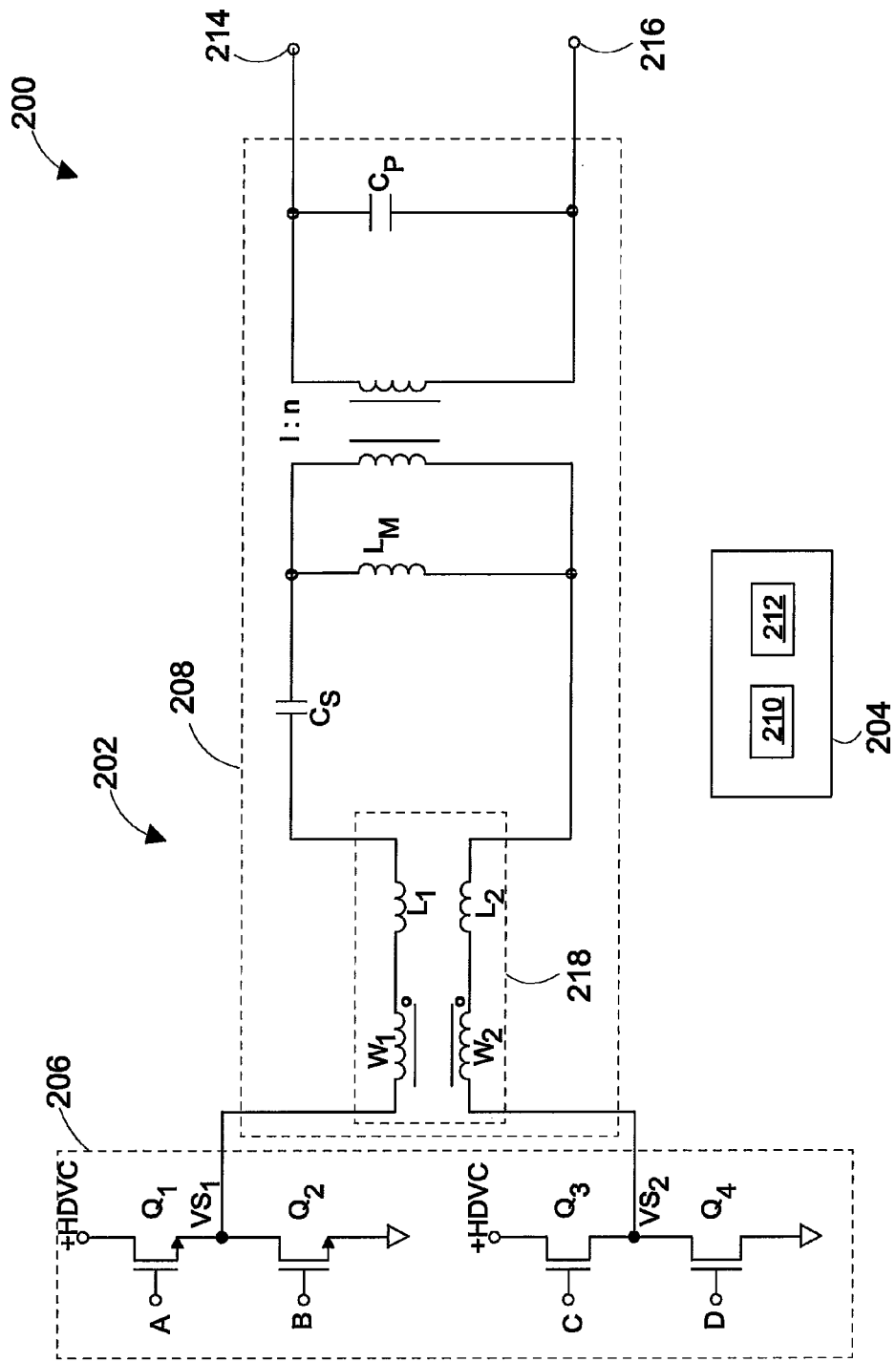
FIG. 2 is a schematic illustration of an electrosurgical generator in accordance with an embodiment of the present disclosure.

Turning to FIG. 2, an electrosurgical generator in accordance with an embodiment of the present disclosure is shown generally as 200. The generator 200 includes suitable input controls (e.g., buttons, activators, switches, touch screen, etc.) for controlling the generator 200. In addition, the generator 200 may include one or more display screens (not shown) for providing the user with variety of output information (e.g., intensity settings, treatment complete indicators, etc.). The controls allow the user to adjust power of the RF energy, waveform, as well as the level of maximum arc energy allowed which varies depending on desired tissue effects and other parameters to achieve the desired waveform suitable for a particular task (e.g., coagulating, tissue sealing, intensity setting, etc.). An instrument (not shown) that may be connected to the generator 200 may also include a plurality of input controls that may be redundant with certain input controls of the generator 200. Placing the input controls at the instrument allows for easier and faster modification of RF energy parameters during the surgical procedure without requiring interaction with the generator 200.

The generator 200 may include a plurality of connectors to accommodate various types of electrosurgical instruments. Further, the generator 200 may operate in monopolar or bipolar modes by including a switching mechanism (e.g., relays) to switch the supply of RF energy between the connectors.

The generator 200 includes a resonant inverter circuit 202 and a pulse width modulation (PWM) controller 204. The resonant inverter circuit 202 includes an H-bridge 206 having FETs Q1, Q2, Q3, and Q4 and a tank 208. The PWM controller 204 includes a processor 210 and a memory 212.

In the resonant inverter circuit 202, the H-bridge 206 is supplied with a positive high voltage direct current (+HVDC). The tank 208 is driven in a full-bridge configuration by the active FET switches Q1, Q2, Q3 and Q4. The PWM controller 208 supplies phase-shifted PWM timing signals to FET switches Q1, Q2, Q3 and Q4 as shown in FIG. 2. FETs Q1 and Q2 provide a voltage $V_{S1}$ to the tank 208 and FETs Q3 and Q4 provide a voltage $V_{S2}$ to the tank 208.

The tank 208 outputs electrosurgical energy to an instrument (not shown) via active terminal 214. In particular, the active terminal 214 provides either continuous or pulsed sinusoidal waveforms of high RF energy. The active terminal 214 is configured to provide a plurality of waveforms having various duty cycles, peak voltages, crest factors, and other suitable parameters. Certain types of waveforms are suitable for specific electrosurgical modes. For instance, the active terminal 214 may provide a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

A return terminal 216 is coupled to a return pad (not shown) for monopolar procedures. Alternatively, the return terminal 216 is electrically coupled to a return electrode (not shown) on an instrument.

Figure 3:
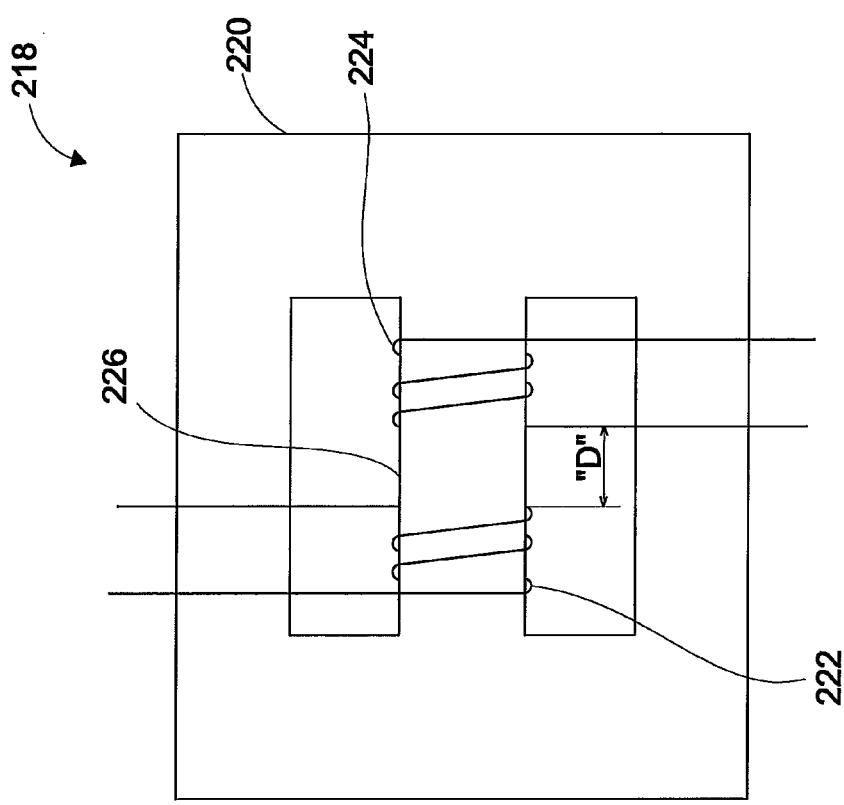
FIG. 3 is an illustration of a common mode choke in accordance with an embodiment of the present disclosure.

In order to impede CM currents generated by the transitions of FET switches Q1, Q2, Q4, and Q4, the tank 208 includes a CM choke 218. A CM choke passes differential currents, currents that are equal but opposite, while blocking CM currents, current that is not opposed by an equal and opposite phase current. The CM choke passes the differential currents in the tank 208 while impeding the CM current. FIG. 3 depicts a schematic representation of the CM choke 218 in accordance with an embodiment of the present disclosure. As shown in FIG. 3, the CM choke 218 includes resonant components $L_1$ and $L_2$. Resonant components $L_1$ and $L_2$ replace the resonant component $L_S$ of the prior art generator architecture shown in FIG. 1 as an energy storage element in order to reduce the number of components in the electrosurgical generator 200. Thus, the CM choke 218 includes the differential inductance needed in the tank 208 while the mutual inductance of the CM choke 218 impedes CM current.

As shown in FIG. 3, CM choke 218 includes a ferrite core 220 such as a PQ2625 FERROXCUBE® ferrite core available from FERROXCUBE (formerly a Philips Components company part of the Yageo Corporation). A primary winding 222 and a secondary winding 224 are wound about a central member 226 of the core 220. Both the primary winding 222 and the secondary winding 224 include 10-15 turns with a negligible gap between turns. The primary winding 222 is wound about the central member 226 in a first direction (e.g., a left handed direction) and the secondary winding 224 is wound about the central member 226 in a second direction opposite from the primary winding 222 (e.g., a right handed direction). The primary winding 222 and the secondary winding 224 are separated by a distance "d". The distance "d" determines the leakage inductance of the CM choke 218. The greater the distance "d", the greater the leakage inductance.

Figure 4:
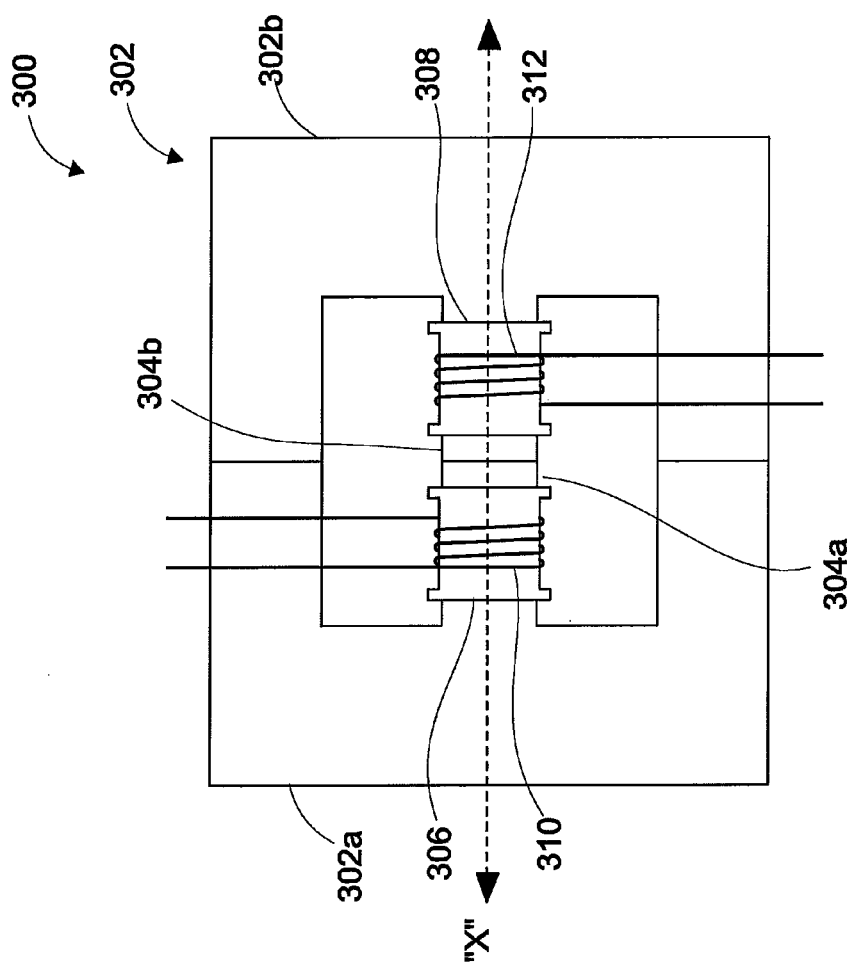
FIG. 4 is an illustration of a common mode choke in accordance with another embodiment of the present disclosure.

FIG. 4 is an illustration of a CM choke 300 in accordance with another embodiment of the present disclosure. CM choke 300 includes a ferrite core 302 manufactured from two separate core halves 302a and 302b. Ferrite core 302 may be an industry standard core such as PQ2625 from FERROXCUBE. Core half 302a includes a central member 304a with a cylindrical member or bobbin 306. Core half 302b also includes a central member 304b having a cylindrical member or bobbin 308. Bobbins 306 and 308 may be moved in a longitudinal direction parallel to an axis "X" defined by central members 304a and 304b.

A primary winding 310 is disposed about bobbin 306. The primary winding 306 includes 10-15 turns with a negligible gap between turns and is wound in a first direction. A secondary winding 312 is disposed about bobbin 308. The secondary winding also includes 10-15 turns with a negligible gap between turns and is wound in a second direction that is opposite the direction of the primary winding. As presented above, the distance "d" between the primary winding and the secondary winding determines the leakage inductance of a CM choke. In the CM choke 300, the distance "d" may be adjusted by moving bobbins 306 and 308 relative to each other thereby changing the distance "d". By adjusting the distance "d", the leakage inductance can be increased or decreased.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An electrosurgical generator comprising:
   a tank configured to output energy;
   an H-bridge configured to drive the tank; and
   a choke configured to impede a common mode current generated by the H-bridge and provide a leakage inductance for the tank, the choke comprising:
      a first core half having a first central member;
      a second core half having a second central member;
      a first bobbin disposed about the first central member;
      a second bobbin disposed about the second central member;
      a primary winding disposed about the first bobbin; and
      a secondary winding disposed about the second bobbin.

2. The electrosurgical generator of claim 1, wherein the primary winding includes 10 to 15 turns.

3. The electrosurgical generator of claim 1, wherein the secondary winding includes 10 to 15 turns.

4. The electrosurgical generator of claim 1, wherein the primary winding is wound in a first direction.

5. The electrosurgical generator of claim 4, wherein the secondary winding is wound in a second direction opposite the first direction of the primary winding.

6. The electrosurgical generator of claim 1, wherein a distance between the primary winding and the secondary winding determines the leakage inductance of the choke.

7. The electrosurgical generator of claim 6, wherein the distance between the primary winding and the secondary winding is adjustable.

8. The electrosurgical generator of claim 7, wherein the distance between the primary winding and the secondary winding is adjustable by moving the first bobbin relative to the second bobbin.

* * * * *